United States Patent
Cunningham

[11] Patent Number: 5,829,443
[45] Date of Patent: Nov. 3, 1998

[54] IMMOBILIZATION DEVICE AND METHOD

[76] Inventor: James Cunningham, 211 Shantilly Shantilly Ct., Danville, Calif. 94526

[21] Appl. No.: 826,561

[22] Filed: Apr. 4, 1997

Related U.S. Application Data

[63] Continuation-in-part of Ser. No. 735,512, Oct. 23, 1996, Pat. No. 5,651,375.

[51] Int. Cl.$^6$ ..................................................... A61B 19/00
[52] U.S. Cl. .......................... 128/869; 128/870; 128/878; 70/16
[58] Field of Search .................................... 128/845, 846, 128/869, 870, 873, 874, 875, 876, 878, 879; 602/19; 5/628, 631, 648; 70/16, 17

[56] References Cited

U.S. PATENT DOCUMENTS

| | | | |
|---|---|---|---|
| 1,047,457 | 12/1912 | Steimer . | |
| 2,006,743 | 7/1935 | Nagle . | |
| 2,324,183 | 7/1943 | Wilson | 70/16 |
| 2,361,328 | 10/1944 | Springer | 5/628 |
| 2,489,828 | 11/1949 | Springer | 5/627 |
| 2,645,922 | 7/1953 | Martin . | |
| 2,766,751 | 10/1956 | Topa | 128/870 |
| 3,399,670 | 9/1968 | Veasey . | |
| 3,669,107 | 6/1972 | Posey | 128/870 |
| 3,732,863 | 5/1973 | Harrington . | |
| 4,004,583 | 1/1977 | Johnson . | |
| 4,173,974 | 11/1979 | Belliveau . | |
| 4,223,670 | 9/1980 | Cramer | 128/870 |
| 4,237,708 | 12/1980 | Bremer . | |
| 4,494,536 | 1/1985 | Latenser . | |
| 4,627,428 | 12/1986 | Brooks . | |
| 4,728,553 | 3/1988 | Daniels . | |
| 4,784,889 | 11/1988 | Daniels . | |
| 4,852,587 | 8/1989 | Share | 128/870 |
| 4,971,073 | 11/1990 | Schneider . | |
| 5,031,629 | 7/1991 | Wolfer . | |
| 5,031,639 | 7/1991 | Wolfer | 128/869 |
| 5,072,725 | 12/1991 | Miller . | |
| 5,275,179 | 1/1994 | Lonardo . | |
| 5,282,483 | 2/1994 | Wang . | |
| 5,316,544 | 5/1994 | McAninch . | |
| 5,387,185 | 2/1995 | Johnson . | |
| 5,400,623 | 3/1995 | Bota . | |
| 5,407,422 | 4/1995 | Matthijs et al. . | |
| 5,421,809 | 6/1995 | Rise . | |
| 5,469,813 | 11/1995 | Peden . | |
| 5,489,259 | 2/1996 | Jacobs et al. . | |
| 5,513,658 | 5/1996 | Goseki . | |

*Primary Examiner*—Michael A. Brown
*Attorney, Agent, or Firm*—William B. Walker

[57] ABSTRACT

The method and device of this invention immobilizes a person in a secure, upright asphyxia-preventing restraining system which includes a leg wrap and shoulder harness, both of which are transparent to x-rays and have the flexibility to safely limit flexing of the legs while immobilizing the upper torso in an erect position without causing damage to the body. It can be easily and safely applied by public safety officers including police or other law enforcement personnel and medical personnel to secure a person against undesired movement while maintaining them in an upright, sitting position which leaves the diaphragm free for natural, unrestrained breathing movement. The asphyxia-preventing restraining device comprises an elongate leg wrap member sized and shaped in the form of a trapezoid to wrap and restrain movement and bending at the knees of the legs of the person to be restrained without injuring the legs. The leg wrap member has at least one tether fastener secured thereto. The upper body restraint comprises a shoulder harness having a front portion, the front portion secured to an adjustable length tether having a distal end, and the distal end of the adjustable length tether having a fastener for securing the tether to the leg wrap. The tether length is shortened to support the person in an upright, asphyxia-preventing position without subjecting the person to physical risk.

19 Claims, 4 Drawing Sheets

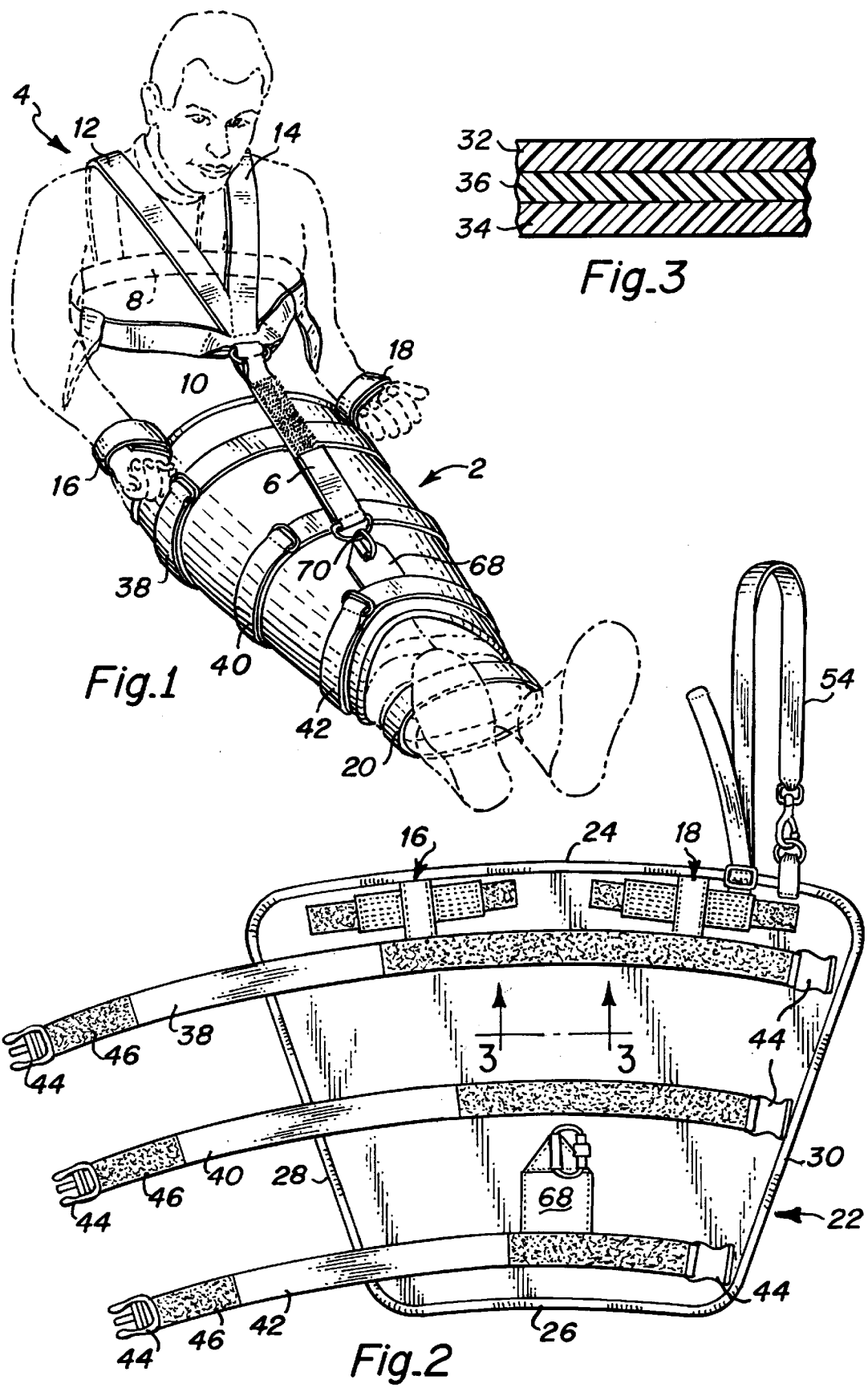

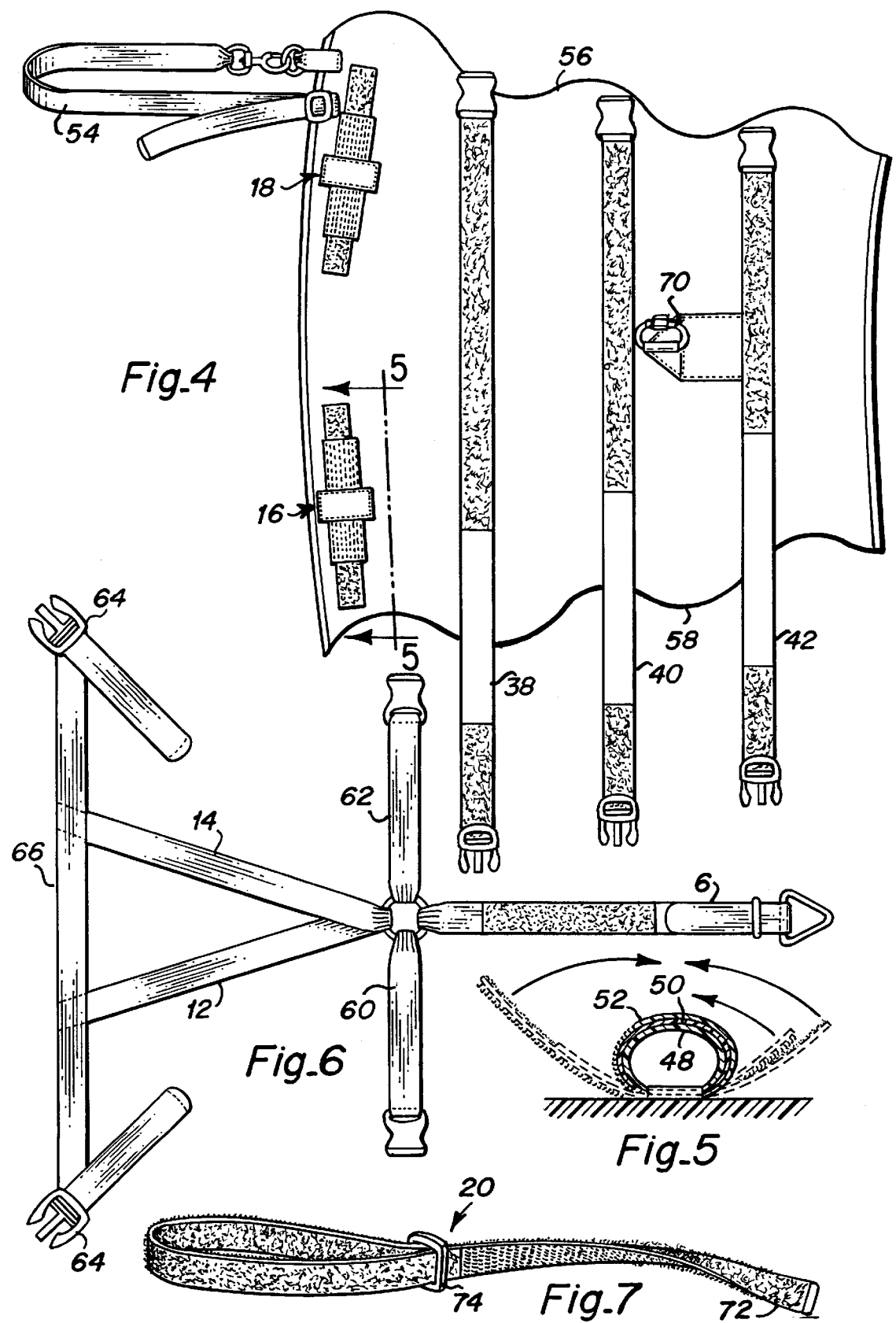

IMMOBILIZATION DEVICE AND METHOD

RELATIONSHIP TO COPENDING APPLICATION

This application is a Continuation-in-Part of application Ser. No. 08/735,512, filed Oct. 23, 1996, now U.S. Pat. No. 5,651,375.

BACKGROUND OF THE INVENTION

The present invention is directed to a device for use by medical, military, and peace officers such as immigration officers, paramedical and law enforcement personnel and corrections officers. The device can be used for restraining psychiatric patients, restraining persons being transported from one location to another in a car, van or ambulance, as a portable detention device, or as a restraint for ambulatory movement of persons requiring restraint during movement. The device of this invention provides safe restraint while supporting the restrainee's body in a position which does not compromise the restrainee's respiratory function.

Prior to this invention, a variety of devices have been used to restrain movement of the arms, hands and/or legs of prisoners and other persons requiring immobilization during capture, transport and custody. The traditional restraining devices for violent restrainees cuff the hands and restrain the legs together behind a person's back in a "hog-tied" configuration as the person lies prone and face-down on a surface. Recent studies have determined this position is the principal cause of a rapidly increasing number of in-custody deaths resulting from positional asphyxia. This risk is present with every prisoner restrained in a face-down position, but is greatly increased when the prisoner is unconscious or mentally disordered, is under the influence of drugs, or has some other condition which impairs mental function or breathing. Irreversible asphyxia and subsequent death in less than one minute following restraint has been documented.

Because law enforcement and other agencies requiring person restraints are legally responsible for maintaining the health and safety of restrained persons under their custody and control, public agencies are desperately seeking restraining devices which can be safely and quickly applied and which do not risk positional asphyxia.

The prior art device shown in FIGS. 8 and 9 is designed to restrain a prisoner's legs in a leg wrap and his hands in cuffs connected to a waist belt. The upright position shown requires a back support (not shown) be provided by a police officer or wall or other object. The waist belt is connected to the leg wrap by two straps to prevent sliding removal of the leg wrap and escape by the prisoner. The configuration requires attachment of the straps and belt to the leg wrap before it is applied since threading the straps into the buckles on the leg wrap is not possible while it is being applied to the prisoner. The device is applied as the person is lying face down in a prone position, and the belt and buckles are under the wrap and prisoner.

This prior art device by itself is unable to secure the prisoner in an upright sitting position and prevent the prisoner from falling to a face-down position threatening asphyxia. A further back support is required to maintain the upright position shown in the figure. Furthermore, since the inflexible straps prevent rearward displacement of the waist belt, rearward rotation of the upper body of the prisoner brings severe and dangerous pressure from the belt to the lower back and kidneys of the prisoner, potentially causing dislocation or rupturing of lower vertebral disks, permanent damage to the spinal column, and severe kidney damage. This risk is particularly high with prisoners who may be jerking and who are not fully conscious or sensitive to pain because of endorphins released in a struggle with police, mind-altering drugs, or mental impairment.

Another deficiency of this prior art device is the use of inflexible metal rods in the leg wrap. These rods bruise the legs of the restrainee, impinging on the common peroneal nerve, and also prevent full x-ray examination of injured persons in custody.

It is desirable to safely restrain persons in custody as quickly as possibly to reduce both the potential for harm to the person being restrained as well as to the arresting officer or medical personnel. For example, handcuffs are conventionally used to restrain hand and arm movements of the person. Other means of restraining arm movements have been employed, such as devices to wrap the torso of the person. U.S. Pat. Nos. 1,047,457; 3,399,670; 4,728,553; 4,852,587; and 5,031,639 disclose various devices which have been employed to provide the desired restraint.

However, in particularly violent circumstances where leg restraints are required, use of leg wraps has led to accusations of police brutality stemming from numerous in-custody deaths due, for example, to asphyxia, particularly positional asphyxiation or respiratory failure. U.S. Pat. Nos. 4,004,583; 4,173,974; 4,237,708; 5,387,185; 5,400,623; and 5,469,813 disclose various means of immobilizing the legs.

OBJECTS AND SUMMARY OF THE INVENTION

It is accordingly an object of this invention to provide an asphyxia-preventing restraining device which can be quickly applied to a prone person to prevent or limit ankle, leg, arm and torso movement of the prone person without endangering the person being restrained or the person applying the device It is a further object of this invention to provide an asphyxia-preventing restraining device comprising a leg wrap/wrist restraint and a separate body support shoulder harness with an adjustable tether which cooperate to hold and restrain a person in an upright position which enables full and unrestrained breathing.

In summary, the method of this invention safely restrains a person in an asphyxia-preventing position using a stiff, flexible leg wrap member sized and shaped to wrap and substantially immobilize the legs of the person. The method comprises the steps of a) immobilizing the legs of the person lying on the leg wrap member by wrapping the leg wrap member around the person's legs and securing the leg wrap member in the wrapped configuration;

b) raising the upper body of the person to a sitting position;

c) applying to the upper body of the person a shoulder harness attached to a forward extending tether, the tether having a tether end at its distal end;

d) attaching the tether end to the leg wrap; and e) adjusting the length of the tether to maintain the person in an upright, asphyxia-preventing position, the shoulder harness having a configuration that provides back support and prevents backward shoulder and upper body rotation beyond the upright asphyxia-preventing position without causing injury to the lower back and kidneys.

The leg wrap can be secured by one or more straps extending around the wrapped legs. The shoulder harness preferably comprises at least one strap extending across the upper back of the person. The leg wrap can optionally include wrist restraints, and the wrists of the person are restrained in the wrist restraints.

In summary, the positional asphyxia-preventing device of this invention for restraining a person in an upright position comprises an elongate leg wrap member (also referred to herein as a "body member") sized and shaped to wrap and restrain movement and bending at the knees of the legs of the person to be restrained, the leg wrap member having a lower portion, at least one tether fastener secured to said lower portion, an upper body restraint comprising a shoulder harness having a front portion, the front portion secured to an adjustable length tether having a distal end, and the distal end of the adjustable length tether having a fastener for securing the tether to the leg wrap.

Preferably, the shoulder harness includes one or more upper support straps and an optional mid-back support strap positioned to extend across the back of a person being restrained; the adjustable length tether includes means for adjusting and securing the tether length; and the leg wrap includes stiffening means for resisting bending of the knees, such as a stiffening layer secured to the leg wrap.

The preferred stiffening layer of the leg wrap is a stiff, flexible thermoplastic polymer such as acrylonitrile-butadiene-styrene plastic which applies the restraining pressure over a large surface area of the legs. Although not as effective, the stiffening means can also include one or more rigid or flexible radiolucent rods having oval, circular or rectangular cross-sections, provided the rods are heavily padded or sandwiched between stiff, flexible layers to spread their pressure over an adequate area to prevent damage to the common peroneal nerve.

The leg wrap member is preferably an elongate, pliable, trapezoid-shaped leg wrap member of such size and shape as to be able to be completely wrapped about the legs of the person to be restrained, said leg wrap member extending from an upper position below the person's waist and above the knee to a lower position between the person's knee and ankle, said leg wrap member having substantially parallel opposed top and bottom edges and non-parallel opposed side edges, the distance between the opposed side edges decreasing toward the bottom of the leg wrap member. The leg wrap member can comprise opposing outer layers of a protective material and an inner unitary flexible stiffening material adapted to immobilize the knee joint and protect the wrapped leg portion of the person; at least two flexible straps sized and shaped to extend about the leg wrap member when wrapped about the legs of the person; and strap securing means to secure each of said straps about said leg wrap member to maintain said leg wrap member in a wrapped position about said person's legs.

The device preferably has wrist restraints attached thereto, the wrist restraints adapted to immobilize the wrists of the person. The leg wrap can have an upper edge and the wrist restraints be attached to the upper edge of said leg wrap member. The wrist restraints can have opposing straps adapted to cooperatively engage to restrain the wrist of said person.

DESCRIPTION OF THE DRAWINGS

FIG. 1 is a prospective view of a person restrained by an assembled device of the invention.

FIG. 2 is a top view of a leg wrap of this invention.

FIG. 3 is a cross-sectional view of the leg wrap of FIG. 2, taken along the line 3—3.

FIG. 4 is a top view of an alternative leg wrap of this invention.

FIG. 5 is a cross-sectional view of a wrist restraint according to this invention.

FIG. 6 is a top view of the shoulder harness of this invention.

FIG. 7 is a prospective view of an ankle restraint which can be used with the leg wrap of this invention.

DETAILED DESCRIPTION OF THE PRESENT INVENTION

Figure 8:
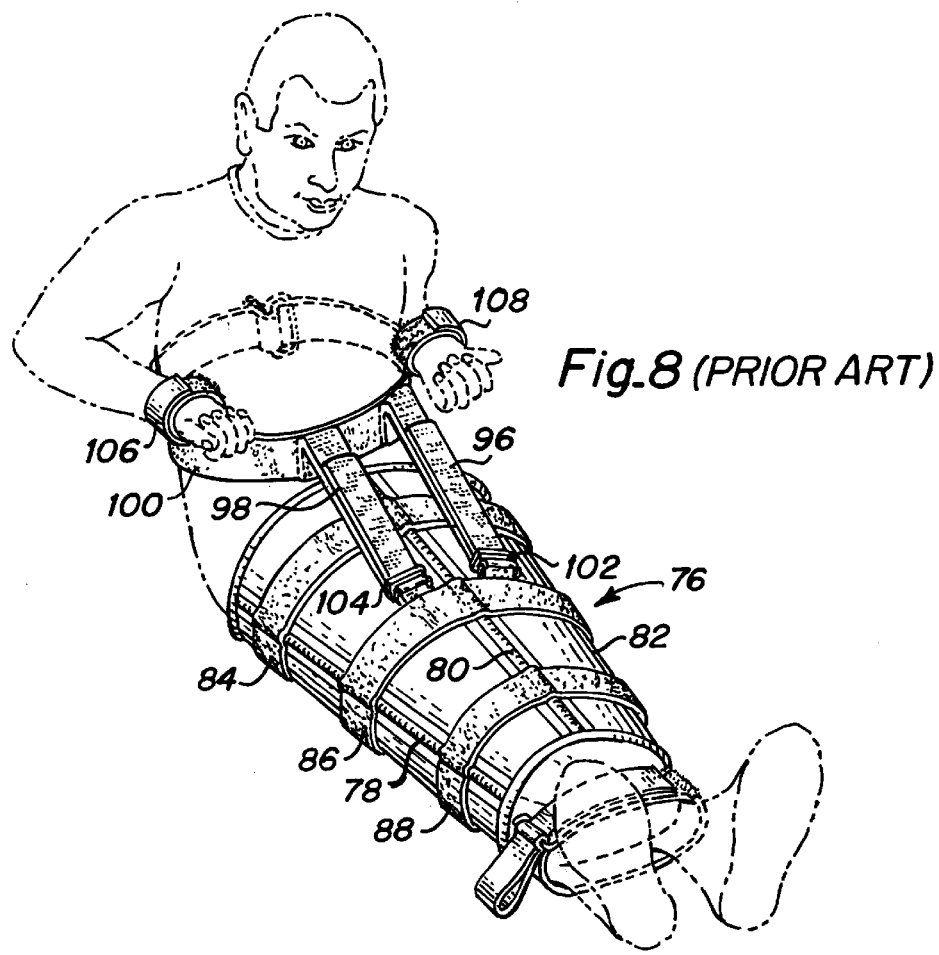
FIG. 8 is prospective view of a prior art restraint device with a waist strap for preventing removal of the leg wrap.

Preventing death in custody is a major priority of all law enforcement and medical agencies and services because an alarming number of persons are dying shortly after they are restrained using conventional procedures. Investigators have determined that the leading cause of such deaths is asphyxia resulting from positioning the decedent's body in an orientation which restricted breathing and/or which led to choking. Irreversible asphyxia has occurred quickly following restraint in some instances, with some deaths occurring within less than one minute following restraint.

The device of this invention is widely acclaimed by law enforcement agencies because it provides a full and effective restraint of the person in custody while maintaining and supporting the person in a position which does not compress the diaphragm and provides free movement of the sternum and chest muscles required for breathing, and it is easily applied without risk by law enforcement and medical personnel. It also positions a person upright to decrease the risk of asphyxia by choking or esophagus obstruction, such as by regurgitating food or liquids. Asphyxia-preventing position, as used herein, is defined to include any upright position which reduces the risk of positional asphyxia caused by obstruction of free movement of the sternum and chest muscles or by choking.

FIG. 1 is a prospective view of a person restrained by an assembled device of the invention. The device of this invention comprises a leg wrap 2, shoulder harness 4, and an adjustable tether 6 connected to the front of the shoulder harness 4. The shoulder harness 4 includes at least one lateral strap 8 which extends across the upper back and connects to the proximal end 10 of the tether 6, and shoulder straps 12 and 14 which extend from the back of the lateral strap 8 over the shoulders to connect to the proximal end 10 of the tether 6.

The combination of the shoulder harness 4 and the length-adjustable tether 6 provide a restraint device which maintains the person in an upright, asphyxia-preventing position, the shoulder harness having a configuration which prevents backward shoulder and upper body rotation beyond the upright asphyxia-preventing position without causing injury to the lower back and kidneys.

The restraint system of this invention also includes wrist restraints 16 and 18, and an optional ankle restraint 20.

FIG. 2 is a top view of a leg wrap of this invention, and FIG. 3 is a cross-sectional view of the leg wrap of FIG. 2, taken along the line 3—3. As shown in FIG. 2, the restraining device of the present invention comprises an elongate body member (leg wrap member) 22 of such size and shape as to be able to be partially or completely wrapped about the legs of the person to be restrained or immobilized. Body member 22 has the shape of a trapezoid, with substantially parallel top and bottom edges 24 and 26, and non-parallel opposed side edges 28 and 30. The distance between the opposed side edges 28 and 30 decreases toward the bottom edge 26 of the body member 22 in order to take into account the fact that less material is required to wrap the legs than to wrap the hip portion of the person.

The body member 22 is sized to extend from an upper position between the person's waist and knee to a lower position between the person's knee and ankle (FIG. 1). As a result, upon being wrapped about the person to be restrained, substantially the entirety of the person's legs may be wrapped and immobilized. By way of non-limiting example, it has been found acceptable for the width of the upper portion of the body member to be at least 38 inches, the width of the bottom portion to be at least 21 inches, and the length of the body member to be at least 26 inches for use in connection with an average size adult.

As depicted in FIG. 3, the body member comprises opposing outer layers 32 and 34 having an inner unitary flexible stiffening layer 36. The outer layers 32 and 34 are formed of a fluid-impermeable material such as a vinyl material which enables the device to be easily cleaned of dirt and body fluids that may be deposited on the device. The stiff, flexible unitary inner layer 36 provides reinforcement and stiffening for the device. The layer 36 also serves to protect the restrained person from harm upon contact with the ground or other objects.

Layer 36 is a unitary layer which provides the necessary stiffening and reinforcement for the body member without the need for stiffening bars or rods. The inclusion of inflexible metal bars or rods has been found to be less desirable because they increase the potential for injury and interfere with x-ray examination of restrained persons. If bar reinforcements are used as stiffeners, they should preferably be flexible, radiolucent (i.e., x-ray transparent) bars having oval, circular or rectangular cross-sections. The bars can be made of a tough, thermoplastic material such as ABS (acrylonitrile-butadiene-styrene) plastic.

The material employed for use as the stiffening/reinforcing layer 36 should be strong enough to resist the application of force, yet flexible enough to permit the body member to be wrapped about the legs of the person to be restrained.

The stiffening, reinforcing material is preferably a tough, stiff, thermoplastic material such as an ABS (acrylonitrile-butadiene-styrene) plastic material. Such materials exhibit a desirable balance of hardness and stiffness. These materials also provide a desirable "pop-open" flex to the body member which causes the body member to lay flat on the ground when unstrapped.

Once wrapped about the legs of the person to be restrained, the body member 22 is held in place by straps attached to the rear portion of the body member 22. As shown in FIGS. 1 and 2, the leg wrap 2 includes multiple straps (preferably at least three) 38, 40 and 42 which extend about the body member 22 and permit attachment to maintain the body member 22 in a wrapped position about the legs. The straps 38, 40 and 42 preferably are positioned on the body member 22 along an upper section of the body member 22, along a midsection of the body member 22, and along a lower portion of the body member 22, respectively.

Each of the straps 38, 40 and 42 includes means to secure the strap about the wrapped body member. At least one of the straps includes a snap-in buckle assembly 44 to facilitate connection of the strap upon the body member being wrapped about the legs of the person. Hook and loop (e.g., Velcro) fasteners 46 may be employed with advantage with the remaining straps. Alternatively, all three of the straps may include a snap-in buckle assembly 44 as means of attachment.

Hand (wrist) restraint means 16 and 18 are provided along the upper portion of the rear of the device. The hand restraint means may simply comprise two opposing straps of material which may be connected together (such as by hook and loop fasteners) to encompass the wrist of the person. Two of such hand restraint means are provided so that each of the hands of the person may be restrained. Desirably, as depicted in FIG. 5, the hand restraint means is comprised of multiple (i.e., two or three) straps which may cooperatively engage to provide the necessary restraint, i.e., a cushioning strap 48, a securing cushioned strap 50, and a locking strap 52, each having cooperatively engagable hook and loop fasteners on opposing surfaces to permit tight engagement of the person's wrists.

Alternatively, handcuff attachment means 54 (FIGS. 2 and 4) can be provided to be optionally connected to handcuffs to restrain movement of the person's hands. Such means 54 may simply comprise a metal ring to which the handcuffs may be attached.

In a second embodiment, as depicted in FIG. 4, the opposed side edges 56 and 58 of the body member are serrated or irregular in configuration and of a design so as to cooperatively mate or assist visual alignment of the body member upon wrapping of the body member about the legs of the person.

Advantageously, the device of the present invention is formed of non-metallic radiolucent materials. The use of such materials enables the person to be medically examined without the need to remove the leg restraint.

FIG. 6 depicts a shoulder harness 4 which may be employed in connection with the restraining device of FIG. 1. The shoulder harness includes opposing straps 60 and 62 which may be connected via buckle means 64 around the person's back and under the armpits. Tether portions 14, 12, and 66 are placed over the person's head. Tether 6 may be attached by suitable means to attachment means 68 (FIG. 1) of the body member to maintain the person in an upright position. As depicted, the triangular ring at the end of tether 6 may be secured within ring 70 (FIG. 1). The length of the tether 6 is adjustable to permit the person to be maintained in an upright position and prohibited from assuming a prone position.

FIG. 7 depicts an ankle restraint strap 20 which may be easily wrapped about the ankles of the person to provide partial restraint prior to use of the body member to restrain the legs. The strap means advantageously includes a hook and loop fastening portion 72 together with a ring portion 74 to permit adjustment of the strap.

In operation, the restraining device of the present invention is designed to be flat and stiff such that it can easily slide under the lower torso of the subject by handling a corner or edge of the body member 22 to provide placement under the legs of the person to be restrained. The body member 22 is then wrapped about the legs and held in place by means of the various strap means 38, 40, and 42. The person's hands may then be immobilized either by use of the hand restraint means 16 and 18 or by handcuffs. The person while restrained may be safely transported in an upright position upon use of the shoulder harness 4 and connection of the harness 4 to the restraining device 2 by means of an adjustable tether 6 from the chest area (secured by a double back strap) to the body member 22. The adjustable tether 6 is shortened to secure the person in the upright position which frees the diaphragm for unrestricted breathing, yet immobilizes the person for transport in a van or other vehicle.

Figure 9:
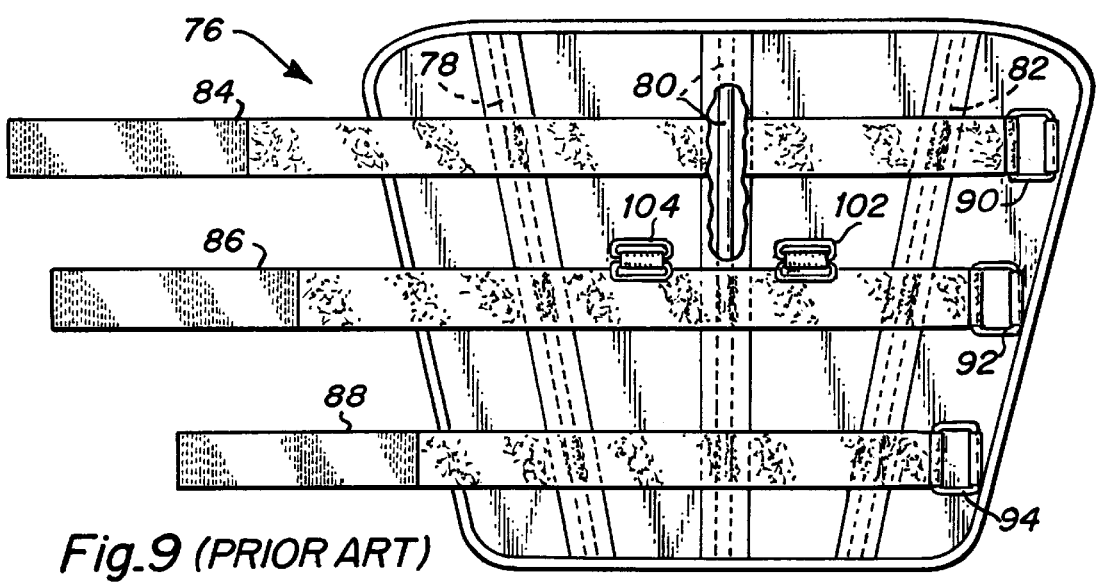
FIG. 9 is a top view of the prior art leg wrap shown in FIG. 8.

FIG. 8 is prospective view of a prior art restraint device with a waist strap for preventing removal of the leg wrap, and FIG. 9 is a top view of the prior art leg wrap shown in FIG. 8. This prior art device comprises a leg wrap 76 with three rigid metal bars 78, 80 and 82 fixed to the wrap. Straps 84, 86 and 88 are secured to respective buckles 90, 92 and 94 to secure the wrap in place around the legs of the person being immobilized. Straps 96 and 98 are secured to the waist belt 100 and to the leg wrap buckles 102 and 104 to prevent sliding removal of the leg wrap by the prisoner. Wrist cuffs 106 and 108 are attached to the waist belt 100.

The person pictured in FIG. 8 is shown in the approximate position required for full breathing, a position which requires use of a back support since the belt cannot support the body in an erect position. Upper body rotation toward the prone position causes the belt 100 to apply severe stress to the lower back and kidneys, risking dislocation or fracture of the spine and severe kidney trauma. The manufacturer recommends use of the device with a back support device to prevent serious injury.

Figure 10:
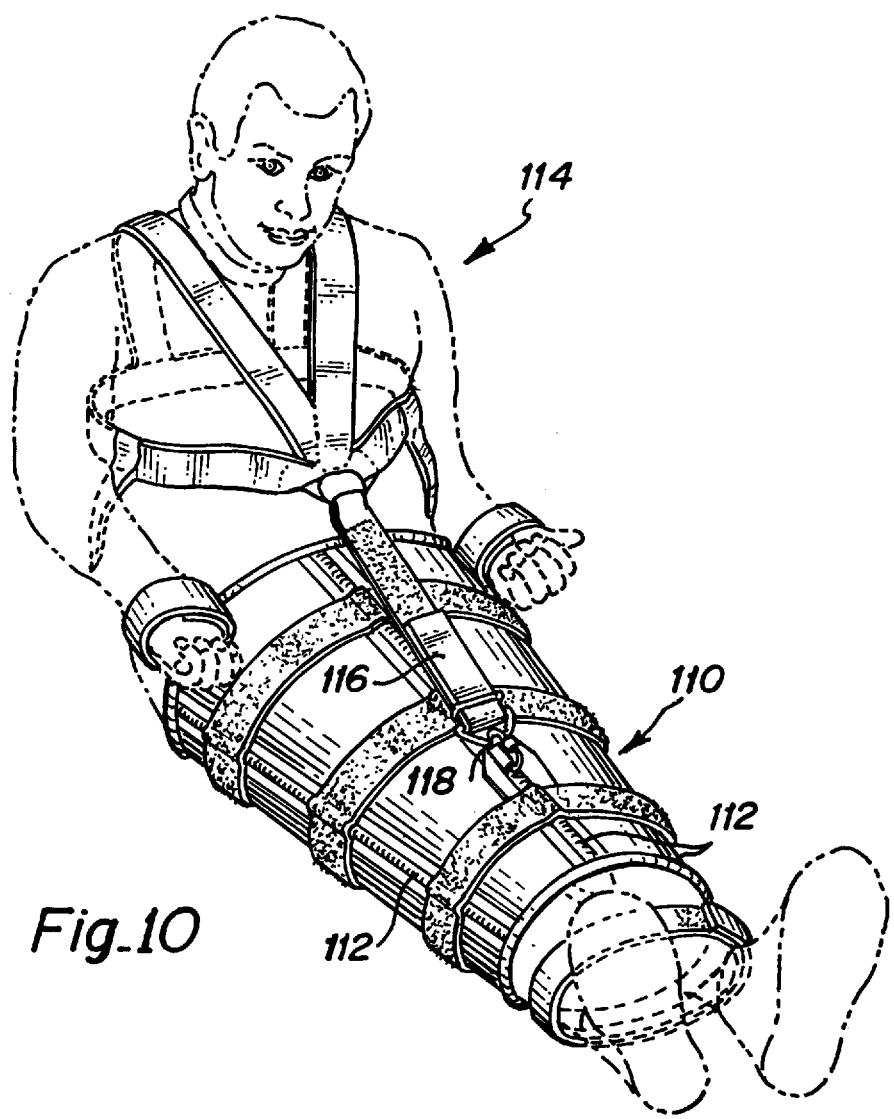
FIG. 10 is a prospective view of an alternative device of this invention combining the shoulder strap and tether assembly with a leg wrap stiffened with rods.

FIG. 10 is a prospective view of an alternative device of this invention combining the shoulder strap and tether assembly with a leg wrap stiffened with rods. In this device, the leg wrap 110 is substantially similar to the prior art leg wrap 76 shown in FIG. 8, with the iron bars 78, 80 and 82 of the leg wrap being replaced by radiolucent, flexible stiffener rods 112, which can be organic polymer materials such as described above. Although not as effective as the flexible stiff members of the embodiment shown in FIG. 1, the stiffening means can also include one or more rigid or flexible radiolucent rods having oval, circular or rectangular cross-sections, provided the rods are heavily padded or sandwiched between stiff, flexible layers to spread their pressure over an adequate area to prevent damage to the common peroneal nerve.

The shoulder harness 114 and tether 116 are substantially the same as shown in FIGS. 1 and 6, the distal end of the tether being connected to a suitable buckle 118. The tether provides both the function of preventing removal of the leg wrap and simultaneously applies harness pressure to maintain the confined person in the upright position required for full breathing.

The invention claimed is:

1. A method for safely restraining a person in an upright, positional asphyxia-preventing position with a stiff, flexible leg wrap member sized and shaped to wrap and substantially immobilize the legs of a person comprising the steps of
   a) immobilizing the legs of the person lying on the leg wrap member by wrapping the leg wrap member around the legs of the person and securing the leg wrap member in the wrapped configuration;
   b) raising the upper body of the person to a sitting position;
   c) applying to the upper body of the person a shoulder harness attached to a forward extending tether, the tether having a tether end at its distal end;
   d) attaching the tether end to the leg wrap; and
   e) adjusting the length of the tether to maintain the person in an upright, asphyxia-preventing position, the shoulder harness having a configuration which prevents backward shoulder and upper body rotation beyond the upright asphyxia-preventing position without causing injury to the lower back and kidneys.

2. A method of claim 1 wherein the leg wrap is secured by one or more straps extending around the wrapped legs.

3. A method of claim 1 wherein the shoulder harness comprises at least one strap extending across the upper back of the person.

4. A method of claim 1 wherein the leg wrap includes wrist restraints and the wrists of the person are restrained in the wrist restraints.

5. An positional asphyxia-preventing restraining device for restraining a person in an upright position preventing asphyxia comprising an elongate leg wrap member sized and shaped to wrap and restrain movement and bending at the knees of the legs of the person to be restrained, the leg wrap member having a lower portion, at least one tether fastener secured to said lower portion;
   an upper body restraint comprising a shoulder harness having a front portion, the front portion secured to an adjustable length tether having a distal end; and
   the distal end of the adjustable length tether having a leg wrap fastener for securing the tether fastener to the leg wrap.

6. An asphyxia-preventing restraining device of claim 5 wherein the shoulder harness includes one or more upper back support straps positioned to extend across the back of a person being restrained.

7. An asphyxia-preventing restraining device of claim 5 wherein the adjustable length tether includes means for adjusting and securing the tether length.

8. An asphyxia-preventing restraining device of claim 5 wherein the leg wrap includes stiffening means for resisting bending of the knees.

9. An asphyxia-preventing restraining device of claim 8 wherein the stiffening means is an inner unitary flexible stiffening layer secured to the leg wrap.

10. An asphyxia-preventing restraining device of claim 9 wherein said inner unitary flexible stiffening layer comprises a thermoplastic polymer.

11. An asphyxia-preventing restraining device of claim 10 wherein the thermoplastic polymer is an acrylonitrile-butadiene-styrene plastic.

12. An asphyxia-preventing restraining device of claim 10 wherein the radiolucent rods have a circular or rectangular cross-section.

13. An asphyxia-preventing restraining device of claim 8 wherein the stiffening means comprises one or more radiolucent rods.

14. An asphyxia-preventing restraining device of claim 8 wherein the wrist restraints comprise opposing straps adapted to cooperatively engage to restrain the wrists of said person.

15. An asphyxia-preventing restraining device of claim 5 wherein the leg wrap member is an elongate, pliable trapezoid-shaped leg wrap member of such size and shape as to be able to be completely wrapped about the legs of the person to be restrained, said leg wrap member extending from an upper position below the person's waist and above the knee to a lower position between the person's knee and ankle, said leg wrap member having substantially parallel opposed top and bottom edges and non-parallel opposed side edges, the distance between the opposed side edges decreasing toward the bottom of the leg wrap member.

16. An asphyxia-preventing restraining device of claim 15 wherein said leg wrap member comprises opposing outer layers of a protective material and an inner unitary flexible stiffening material adapted to immobilize the knee joint and protect the wrapped leg portion of the person.

17. An asphyxia-preventing restraining device of claim 16 including at least two flexible straps sized and shaped to extend about the leg wrap member when wrapped about the legs of the person and strap securing means to secure each of said straps about said leg wrap member to maintain said leg wrap member in a wrapped position about said person's legs.

18. An asphyxia-preventing restraining device of claim 5 having wrist restraints attached thereto, the wrist restraints adapted to immobilize the wrists of the person.

19. An asphyxia-preventing restraining device of claim 18 wherein the leg wrap member has an upper edge and the wrist restraints are attached to the upper edge of said leg wrap member.

* * * * *